United States Patent
Hall et al.

(10) Patent No.: US 10,295,511 B2
(45) Date of Patent: May 21, 2019

(54) MICROFABRICATED STAGED PRECONCENTRATION AND PARALLEL COLUMN FOR GAS CHROMATOGRAPHY

(71) Applicants: David R. Hall, Provo, UT (US); Dan Allen, Springville, UT (US); Steven Butala, Provo, UT (US); Terrece Pearman, Draper, UT (US)

(72) Inventors: David R. Hall, Provo, UT (US); Dan Allen, Springville, UT (US); Steven Butala, Provo, UT (US); Terrece Pearman, Draper, UT (US)

( * ) Notice: Subject to any disclaimer, the term of this patent is extended or adjusted under 35 U.S.C. 154(b) by 412 days.

(21) Appl. No.: 15/380,064

(22) Filed: Dec. 15, 2016

(65) Prior Publication Data
US 2018/0172646 A1    Jun. 21, 2018

(51) Int. Cl.
*B01D 53/02* (2006.01)
*G01N 30/14* (2006.01)
*G01N 30/06* (2006.01)
*G01N 30/02* (2006.01)
*G01N 30/00* (2006.01)

(52) U.S. Cl.
CPC ..... *G01N 30/14* (2013.01); *G01N 2030/0095* (2013.01); *G01N 2030/025* (2013.01); *G01N 2030/062* (2013.01); *G01N 2030/143* (2013.01)

(58) Field of Classification Search
CPC ..... G01N 2030/0095; G01N 2030/025; G01N 2030/062; G01N 2030/143; G01N 30/14
See application file for complete search history.

(56) References Cited

U.S. PATENT DOCUMENTS

| | | | | |
|---|---|---|---|---|
| 8,771,613 B2* | 7/2014 | Martin | ................ | G01N 1/405 422/400 |
| 9,599,547 B2* | 3/2017 | Rafferty | ................ | G01N 1/405 |
| 2004/0194628 A1* | 10/2004 | Mitra | ................ | G01N 30/12 96/101 |
| 2005/0100959 A1* | 5/2005 | Sinbanda | ................ | G01N 30/14 435/7.1 |
| 2009/0090197 A1* | 4/2009 | Finlay | ................ | G01N 1/2214 73/863.12 |
| 2010/0236341 A1* | 9/2010 | Martin | ................ | G01N 1/405 73/863.12 |

(Continued)

*Primary Examiner* — Christopher P Jones (57) ABSTRACT

We disclose a microfabricated device for both extracting and preconcentrating samples for gas chromatography analysis. The device includes a conduit with at least two sections and multiple ports which may be connected to multiple gas chromatography columns. The inner surface of the conduit may be coated with multiple sorbents which bind volatile analytes with different affinities. The sections of the conduit may be divided by a thermal barrier which inhibits heat transfer between sections. Consequently, each section may be independently heated to encourage desorption of volatile analytes. The disclosed device separates and concentrates volatile analytes into different pools according to their chemical and physical properties before they enter a gas chromatography column that is optimized for that pool. The device reduces the amount of heat and time needed to perform gas chromatography analysis as well as avoids the need for purified gas sources typically used for the moving phase.

20 Claims, 12 Drawing Sheets

(56) References Cited

U.S. PATENT DOCUMENTS

| | | | |
|---|---|---|---|
| 2011/0010107 A1* | 1/2011 | Fedder | G01N 27/127 |
| | | | 702/22 |
| 2013/0186174 A1* | 7/2013 | Seo | G01N 30/00 |
| | | | 73/23.35 |
| 2014/0260535 A1* | 9/2014 | McGill | G01N 30/74 |
| | | | 73/23.37 |
| 2016/0103104 A1* | 4/2016 | Gianchandani | B01L 3/502707 |
| | | | 73/23.41 |
| 2018/0164260 A1* | 6/2018 | Agah | G01N 30/60 |

* cited by examiner

MICROFABRICATED STAGED PRECONCENTRATION AND PARALLEL COLUMN FOR GAS CHROMATOGRAPHY

BACKGROUND

Field of the Invention

This invention relates to systems and methods for analyzing and separating chemical compounds, particularly using gas chromatography.

Background of the Invention

Sample preparation is required to prior to separation of volatile compounds using gas chromatography (hereinafter, "GC"). First, volatile compounds must be extracted from the sample if the sample is not already gaseous. One such method of extraction of volatile compounds is headspace sampling. In headspace sampling, the sample is heated to promote the evolution of gas phase compounds from the liquid phase into the headspace at the top of the partially filled vial. The second required step is preconcentration which is currently performed by using a sorbent which adsorbs volatile compounds from the sample.

Sparging is a method of combining extraction and preconcentration. In sparging, a gas is bubbled through the liquid sample to promote evolution of volatile compounds from the liquid by Le Chateleir's principal. The bubbled gas passes through a preconcentrator which adsorbs the volatile compounds exhausted from the sample.

Another method for preconcentrating samples for GC is solid phase microextraction (hereinafter, "SPME"). In SPME, a sorbent-coated fiber sheathed in a hollow needle is inserted into the headspace and the fiber is extended into the headspace. The sorbent (or multiple sorbents) on the surface of the fiber constitute the solid phase. The sorbent comes into equilibrium with the volatile compounds in the headspace and is removed from the headspace, the sorbent is heated to eject the adsorbed volatiles into a GC column. It is significant that the partitioning of analytes between the liquid and gas phases in the headspace is related to the concentration of ionic salts in solution which may reduce the solubility of the analytes. Also, different sorbents have different affinities for any given volatile analyte. Consequently, SMPE is not a best practice for quantitative analysis unless care is taken to calibrate the measurement for a particular sample type.

In contrast to SPME, the needle trap technique samples headspace and is quantitative without the need for precalibration. The needle trap moves air from the headspace through a preconcentrator needle in one direction. The inner surface of the preconcentrator needle is typically coated with at least two sorbents of differing affinity for volatile analytes. The flow is then reversed for injection into the gas chromatograph. The needle is heated at relatively high temperatures which causes the sorbents to release the volatile analytes.

The extracted and preconcentrated sample is then separated by GC. This requires a moving phase which comprises an inert gas. Examples of suitable inert gases are nitrogen and helium. The volatile analytes which have a greater affinity for the column walls move more slowly through the column as the mobile phase passes through than those with a lesser affinity for the column walls. The higher affinity volatile analytes may be released more quickly by heating the column. This step reduces the time of the GC run.

It is desirable to adapt GC technology for use in environments outside the laboratory or clinic. The steps of using an inert gas and high temperatures used in conventional techniques present problems with regard to adapting GC to use in a ubiquitous environment, such as a home or in a mobile situation. One is the general lack of an inter mobile phase such as helium or nitrogen gases. A mobile gas chromatograph must either separate oxygen and potential volatile contaminants from the moving phase or run a filtered atmospheric gas mixture through the column. Oxygen may react with both the volatile analytes and the stationary phase of the column at the elevated temperatures necessary to elute analytes with higher affinity to the column in a reasonable amount of time. This has been known to degrade the sample, and sometimes, the column.

Another problem with adapting GC technology to ubiquitous environments is the length of time required to complete separation using standard GC techniques. The length of time required to complete a GC run using current technology may be impractical for the applications in which GC is used in a ubiquitous environment. A solution to address separation of the higher molecular weight volatile analytes that adhere relatively strongly to the GC column is needed to adapt GC technology to a ubiquitous environment.

BRIEF SUMMARY OF THE INVENTION

We disclose a novel microfabricated device for both exhausting and preconcentrating samples in preparation for analysis by GC. Microfabrication results in a thinner, smaller device with the advantages that are associated with thin column walls and ease of manufacturing. The device includes a conduit with multiple sections. The inner surface of each section is coated with at least one sorbent and the sorbents in each section differ in their relative ability to bind volatile analytes. The different binding affinities may be a function of either the polarity or molecular weight of the volatile analytes. In some embodiments, the inner surface of one or more sections is coated with multiple sorbents, each with a different volatile analyte binding activity.

Some embodiments include a thermal barrier that may be made from a thermal insulating material. The thermal barrier may be placed adjacent to the wall of the conduit, within the wall of the conduit, or the substrate used to manufacture the conduit as part of the microfabrication process may include a thermal insulating material. The thermal barriers inhibit heat transfer between sections. Consequently, individual sections may be heated without heating the other sections to sequentially encourage desorption of adsorbed volatile analytes.

The device may include multiple gas analyzer ports which may be connected to multiple GC columns. The device may be configured to allow a user to desorb volatile analytes selectively and sequentially into separate pools which may then be diverted into a GC column that is optimal for separating the contents of that pool. The enhanced preconcentration and separation of the contents in the sample may reduce the amount of heat required to run the GC analysis. The amount of time may also be reduced and the need for purified gas for moving phase gas may be eliminated. These features are conducive to adapting GC to ubiquitous environments including the home and mobile GC units.

DETAILED DESCRIPTION OF THE INVENTION

Disclosed herein is a microfabricated device for extracting and preconcentrating volatile analytes prior to gas chromatography. The device both extracts and preconcentrates volatile analytes prior to separation by GC. The device further separates volatile analytes into different pools which may separately be exhausted from the device into a different gas chromatography column. Therefore, each separate pool of preconcentrated analyte may be injected into a GC column that is optimal for separating the contents of that pool. Consequently, the high temperatures that are often needed to perform GC analysis may not be necessary to achieve adequate separation. In addition, the purified gases, which may be helium or nitrogen, may not be needed to perform the separation. In contrast, a filtered atmospheric gas may be used as a moving phase instead. These features contribute to the increased speed at which the GC run may be completed. The reduced temperatures, lack of a need for purified gas for the moving phase, and reduced time for analysis are features which make this device amenable to GC analysis in a ubiquitous environment such as the home or in a mobile device.

The disclosed device may include a conduit. The conduit may include a first, intermediate, and second section. Each section may include a wall with an outer surface and an inner surface. Each inner surface may be coated with a sorbent that has a binding activity for volatile analytes. Each sorbent may possess a different binding activity. The binding activities may be based on molecular properties of the volatile analytes that may include polarity or molecular weight. In some embodiments, each section may contain multiple unique sorbents. For example, the first section may contain two different sorbents and the second section may contain two different sorbents, and each sorbent may have a different binding activity for volatile analytes than the other.

The disclosed device may include a section valve which may be positioned within the conduit between the first section and the second section. The section valve may block movement of volatile analytes and other materials between the first section and the second section when the section valve is in a first position. Alternatively, the section valve may allow movement of volatile analytes and other materials between the sections when the section valve is in a second position.

The device may include a moving phase port for injecting a moving phase gas into the conduit. The moving phase gas causes the volatile analytes to desorb from the sorbents as it passes through the conduit. The device may also include at least one gas analyzer port which connects the device to a GC column. Some embodiments include a plurality of gas analyzer ports. Each of the one or more gas analyzer ports may include a valve to regulate the flow of material between the device and the gas chromatograph. The valve may comprise any of a variety of valve designs known in the art including but not limited to, a check valve or an actuated valve. In some embodiments, the moving phase port is positioned within the intermediate section of the conduit. Moving phase gas injected into a moving phase port located within the intermediate section may move in both directions along the conduit. Specifically, the moving phase gas may simultaneously move both toward the first section and the second section.

By including multiple gas analyzer ports, the sample may simultaneously be analyzed by different GC columns. The section which collected a pool of volatile analytes that is best analyzed by a particular column may be connected to that column through the gas analyzer port that is connected to that section of the conduit.

The device may include an entrance port for injecting samples to be analyzed. For example, the sample may be volatile material collected from the headspace of a liquid sample.

The device may further include an exit port. The exit port may be used to exhaust the contents of a sample that has been injected into the device after the sample has passed over the sorbents. The volatile analytes adsorb to the sorbents and the remaining material exits the device through the exit port. The exit port may be located at the end of the first section or the second section. In other words, the exit port may be located at either end of the conduit. The exit port may include a valve that may be a check valve, an actuated valve, or other type of valve known in the art.

In some embodiments, the device includes a heater. The heater may be connected to the first section or the second section. Some embodiments may include two heaters, each connected to one of the first or second sections. Alternatively, some embodiments include a single heater connected to both sections which is configured to independently heat the first or second section.

Some embodiments of the device include a thermal insulating material. The thermal insulating material maybe position within the first section wall and the second section wall at the point where they intersect thus creating a thermal barrier between the two sections. The thermal insulating material inhibits heat transfer between the two sections when one section is heated and the other is not. The thermal insulating material may be made of a variety of materials known in the art including, but not limited to, plastic, glass, and insulating ceramic. The substrate used in microfabrication may also include thermal insulating material.

The disclosed device may be manufactured using microfabrication techniques. Accordingly, the conduit is created by applying a substance that will comprise the walls and inner surfaces of the conduit to a substrate. The conduit may be formed by removing the walls and inner surfaces from the substrate or by leaving the walls and inner surface adhered to the substrate then placing a cap over the substrate or the added walls and inner surfaces.

The substrate may comprise glass, quartz, ceramic photopatternable glass/ceramic, silicon, or other materials known in the art for use as substrates in microfabrication. The substrate thickness may be less than about 2 mm or, in some embodiments, less than about 1 mm. The diameter of the resulting conduit may be less than about 0.5 mm or, in some embodiments, less than about 0.250 mm. The conduit may also be manufactured by additive microfabrication techniques. These include, but are not limited to, photopatternable walls, cross-linked photoresist, nano stamp lithography, or micro stamp lithography.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

Figure 1A:
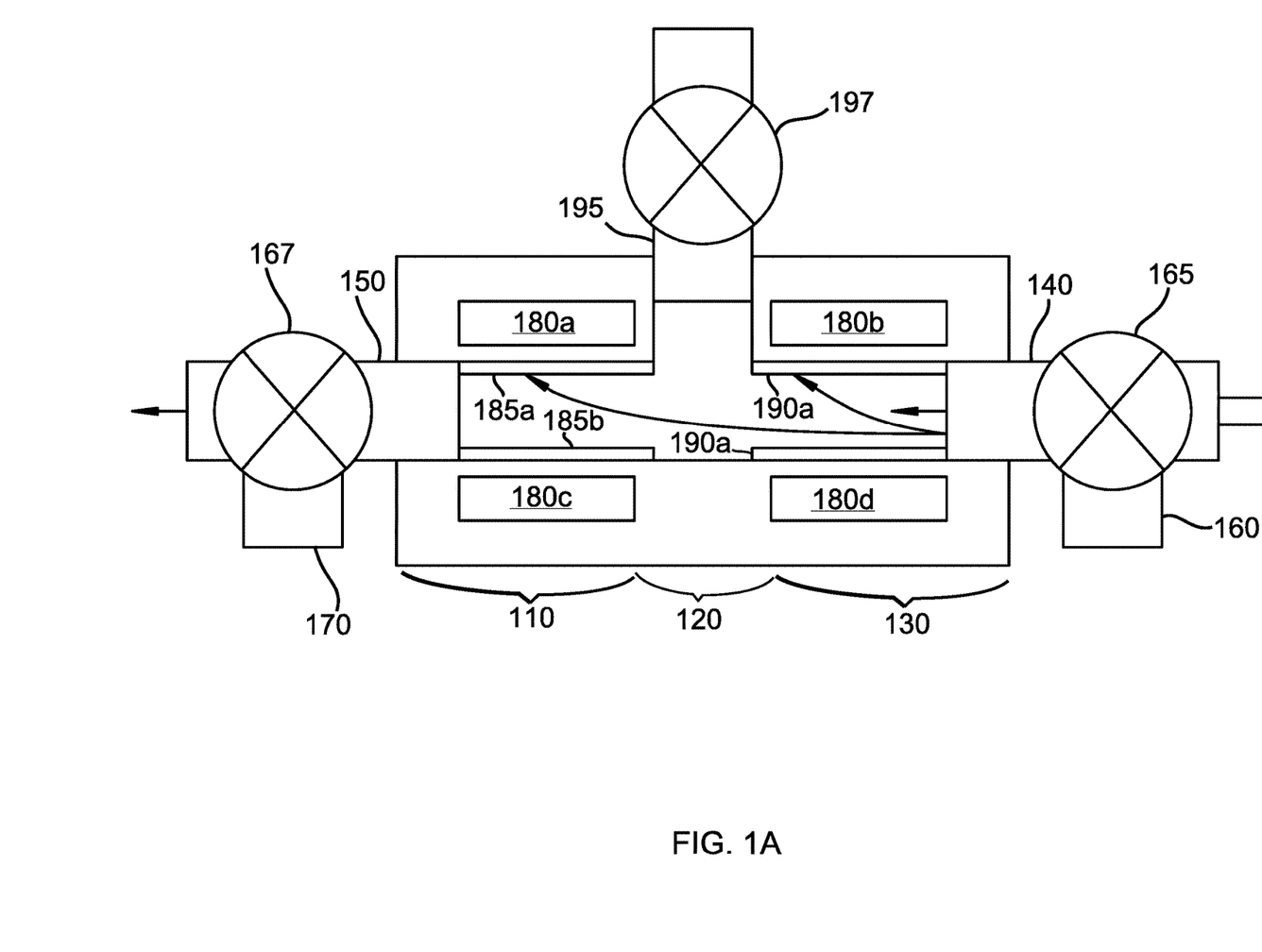
FIG. 1A illustrates a cross-section of an embodiment of the device with a single sorbent in each section of the conduit.

Referring now to the drawings, FIG. 1A illustrates an embodiment of the device comprising a conduit. The conduit includes first section 110, intermediate section 120, second section 130. The inner walls of first section 110 are coated with first sorbent 185a and 185b. The inner walls of second section 130 are coated with second sorbent 190a and 190b. First sorbent 185a and 185b has a different binding affinity for volatile analytes than second sorbent 190a and 190b. Entrance port 140 is connected to the conduit at second section 130 and may be used to inject samples to be analyzed. Entrance port valve 165 is included in this embodiment to close off entrance port 140 when not in use. Exhaust port 150 is connected to first section 110 and provides an exit port for material that has passed through the conduit but not adsorbed to the sorbents. The embodiment of FIG. 1A further includes moving phase port 195 through which a moving phase gas may be injected to desorb the volatile analytes from the sorbents and direct them into the gas chromatograph columns. Moving phase port 195 includes moving phase valve 197 which may be closed when the conduit is being loaded with sample to prevent material from escaping through moving phase port 195 without traveling through the length of the conduit. The device further includes first gas analyzer port 160 and second gas analyzer port 170 each of which is configured to connect to a GC column. As will be described in more detail herein, different pools of analytes adsorb to the different sorbents and then may be selectively directed through either first gas analyzer port 160 or second gas analyzer port 170 for separation by the most optimal GC column. First gas analyzer port 160 includes valve 165 and second gas analyzer port 170 includes valve 167. Valve 165 enables the user to either direct the flow of injected sample material from entrance port 140 into second section 130 without escaping through first gas analyzer port 160 or to direct the flow from second section 130 into first gas analyzer port 160 without escaping through entrance port 140. Likewise, second gas analyzer port 170 enables the user to either direct the flow of material from first section 110 through exhaust port 150 without escaping into gas analyzer port 170 or to direct the flow of material from first section 110 through second gas analyzer port 170 without escaping through exhaust port 150.

In the embodiment shown in FIG. 1A, exhaust port 150 and second gas analyzer port 170 are combined in a t-connector pipe. Exhaust port 150 comprises the horizontal section of the t-connector pipe while second gas analyzer port 170 comprises the vertical section of the t-connector pipe. Each port is individually opened while the other is close by actuating valve 167. Similarly, entrance port 140 and first gas analyzer port 160 are combined in a t-connector pipe. Entrance port 140 comprises the horizontal section of the t-connector pipe while first gas analyzer port 160 comprises the vertical section of the t-connector pipe. Each port is individually opened while the other is close by actuating valve 165.

Figure 1B:
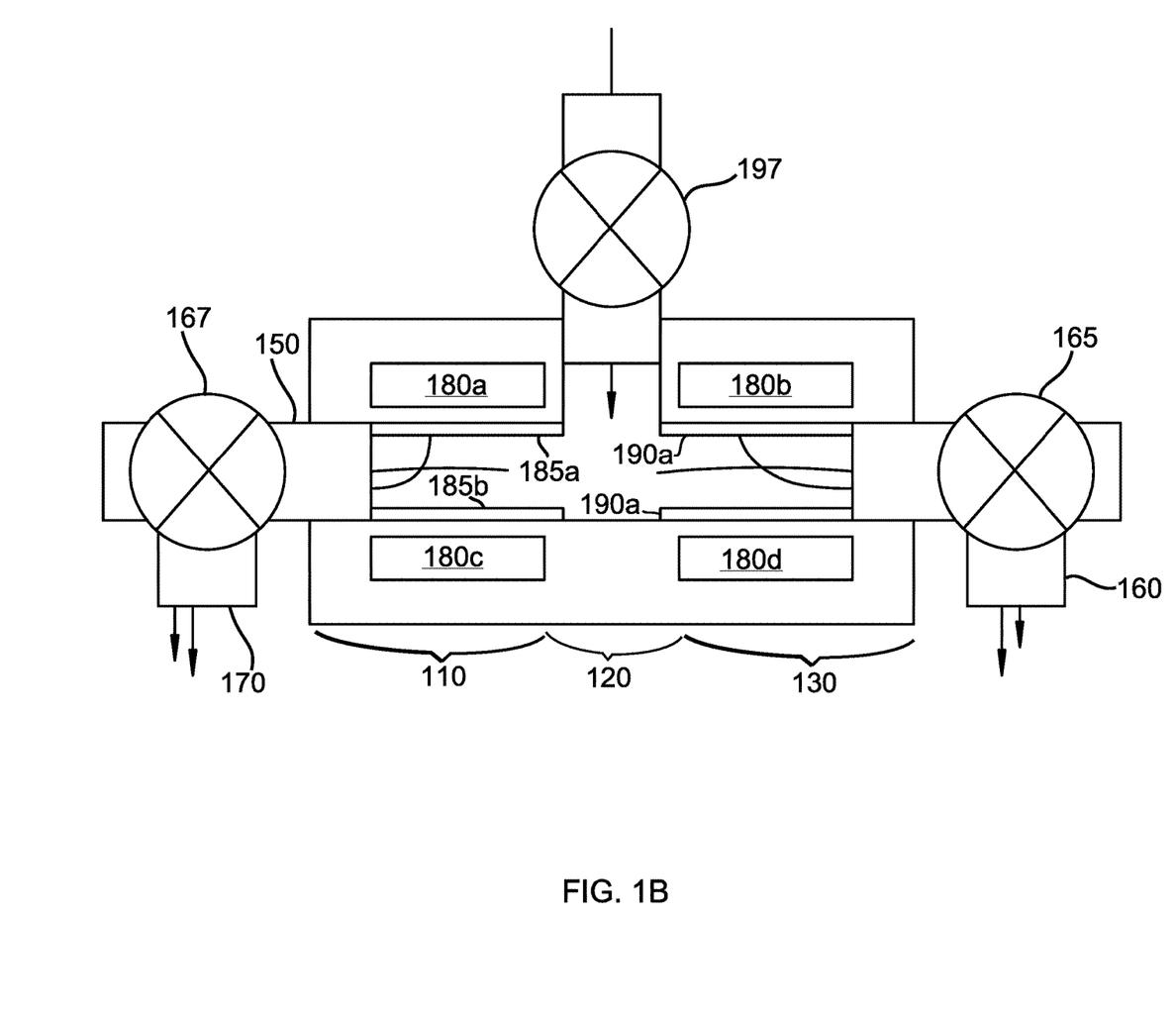
FIG. 1B illustrates a cross-section of the embodiment of FIG. 1 as volatile analytes are being exhausted into GC columns.

FIG. 1B illustrates the embodiment of FIG. 1A in the process of being exhausted into the two GC columns. The volatile analytes in the sample have been adsorbed to the sorbents. The downward pointing arrow illustrates moving phase gas is being injected into the conduit through moving phase port 195. In this embodiment, moving phase port 195 is positioned in intermediate section 120, which comprises the point of connection between first section 110 and second section 130, so that the moving phase gas travels through both first section 110 and second section 130 to desorb volatile analytes from both sections. Volatile analytes that desorb from first sorbent 185a and 185b travel with the moving phase gas through second gas analyzer port 170. Volatile analytes that desorb from second sorbent 190a and 190b travel with the moving phase gas through first gas analyzer port 160. Because the volatile analytes that desorb from first sorbent 185a and 185b are either a different size (molecular weight) or polarity than those that desorb from second sorbent 190a and 190b, a different type of GC column optimally separates them. This mechanism enables separation of the volatile analytes prior to GC analysis which may improve the efficiency of separation within the GC columns and shortens the time of analysis.

FIGS. 1A and 1B further illustrate thermal insulating material 180a, 180b, 180c, and 180d within the walls of the conduit. In some embodiments, the thermal insulating material may be on the outside of the conduit. The thermal insulating material may be included in the substrate used during microfabrication of the conduit. The thermal insulator inhibits heat transfer between the sections. Thus, one section may be heated to cause the volatile analytes to desorb from the sorbent more quickly without transmitting the heat to the adjacent section.

In some embodiments, the thermal insulating material creates a thermal barrier between sections of the conduit. The thermal barrier may be a region that includes a material of lower thermal conductivity disposed within a removed portion of the substrate. In other embodiments, the thermal barrier comprises a physical constriction formed by removing material from the microfabrication substrate.

Figure 2:
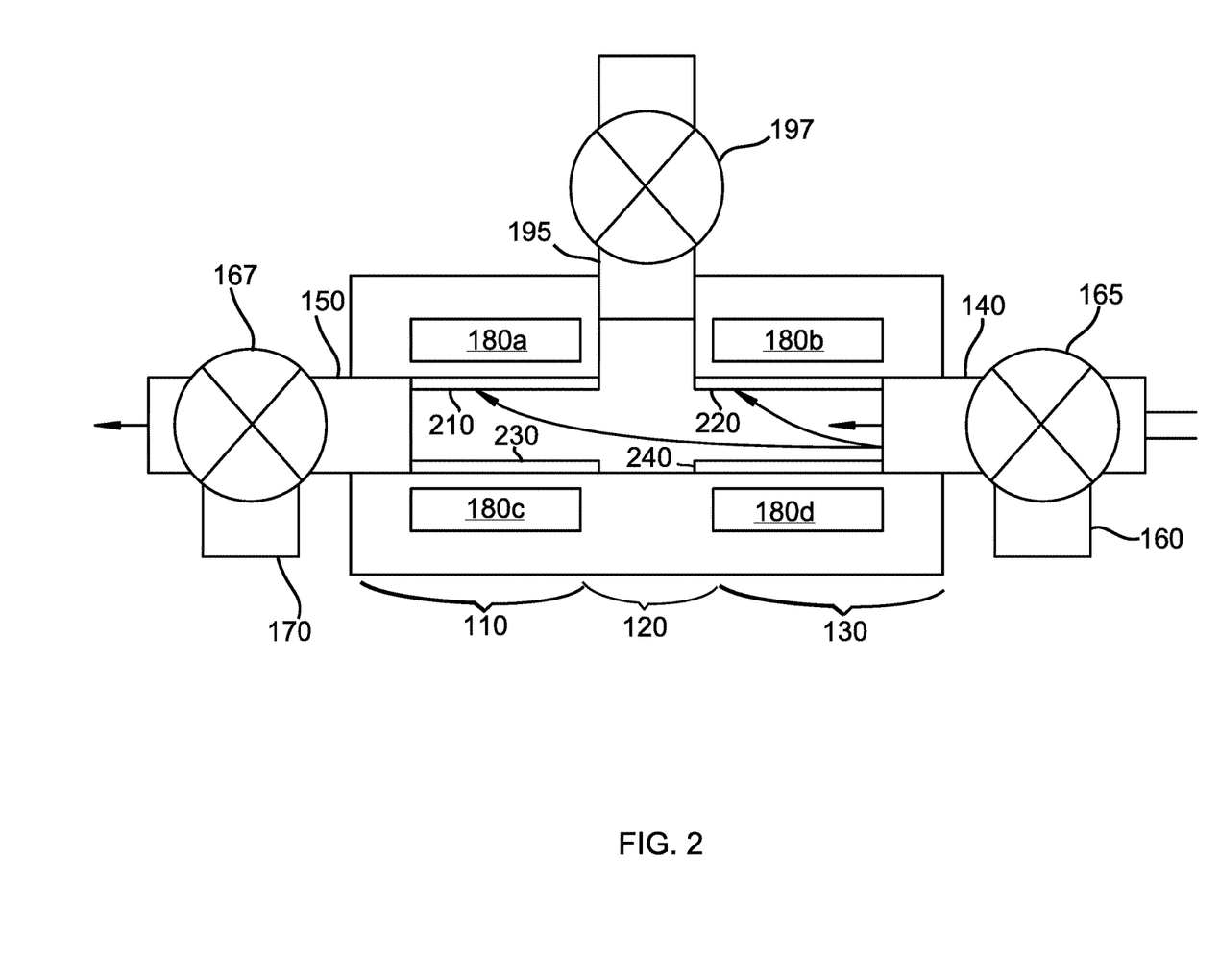
FIG. 2 is a cross-section of an embodiment of the device with two sorbents in each of the first and second sections of the conduit.

FIG. 2 illustrates a modification of the embodiment shown in FIGS. 1A and 1B in which first section 110 includes two different sorbents, sorbent 210 and sorbent 230 and second section 130 includes two different sorbents, sorbent 220 and sorbent 240. Each of sorbents 210, 220, 230, and 240 may possess a different binding affinity for volatile analytes.

Figure 3:
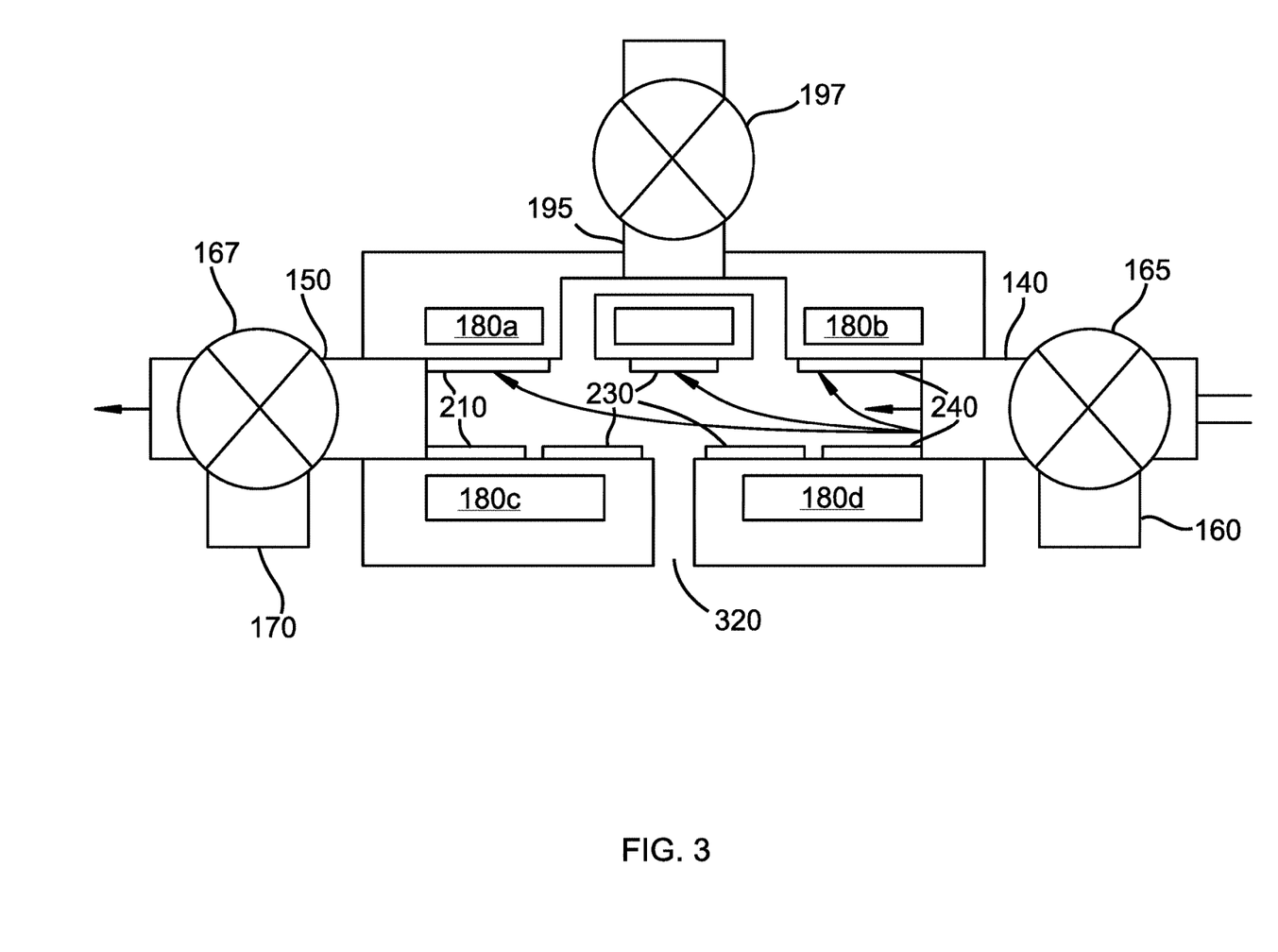
FIG. 3 illustrates an embodiment of the device which includes more than two gas analyzer ports.

FIG. 3 illustrates an embodiment of the invention which includes more than two gas analysis ports. Consequently, the device may separate the volatile analytes into more than two pools and may divert each pool into a separate GC column. The embodiment shown in FIG. 3 includes multiple channels leading from moving phase port 195. For example, if the number of gas analyzer ports is "N", the number of channels leading from moving phase port 195 may be "N−1".

Figure 4A:
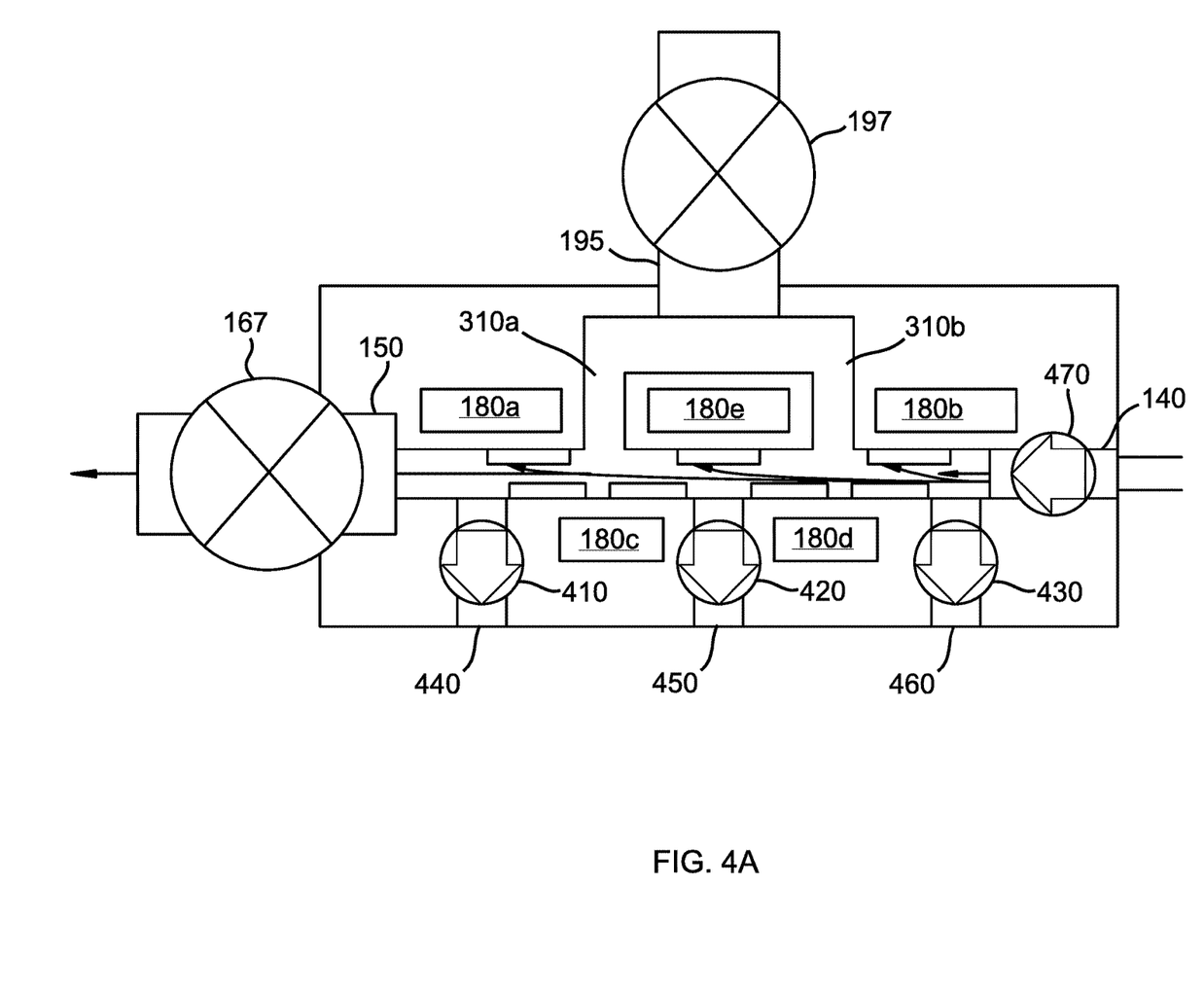
FIG. 4A illustrates a cross sectional view of an embodiment of the device which includes internal check valves during preconcentration.

FIG. 4A illustrates an embodiment of the device during preconcentration of a sample. The embodiment of FIG. 4A includes multiple gas analyzer ports, including gas analyzer port 440, 450, and 460. Each gas analyzer port includes a check valve. These include check valve 410 within gas analyzer port 440, check valve 420 within gas analyzer port 450, and check valve 430 within gas analyzer port 460. Entrance port 140 includes check valve 470 in this embodiment. FIG. 4A uses arrows to illustrate movement of a sample, which may be from a headspace, through entrance port 140 and the volatile analytes adsorbing to the different sorbents. The remaining contents of the sample exits the conduit through exhaust port 150.

Figure 4B:
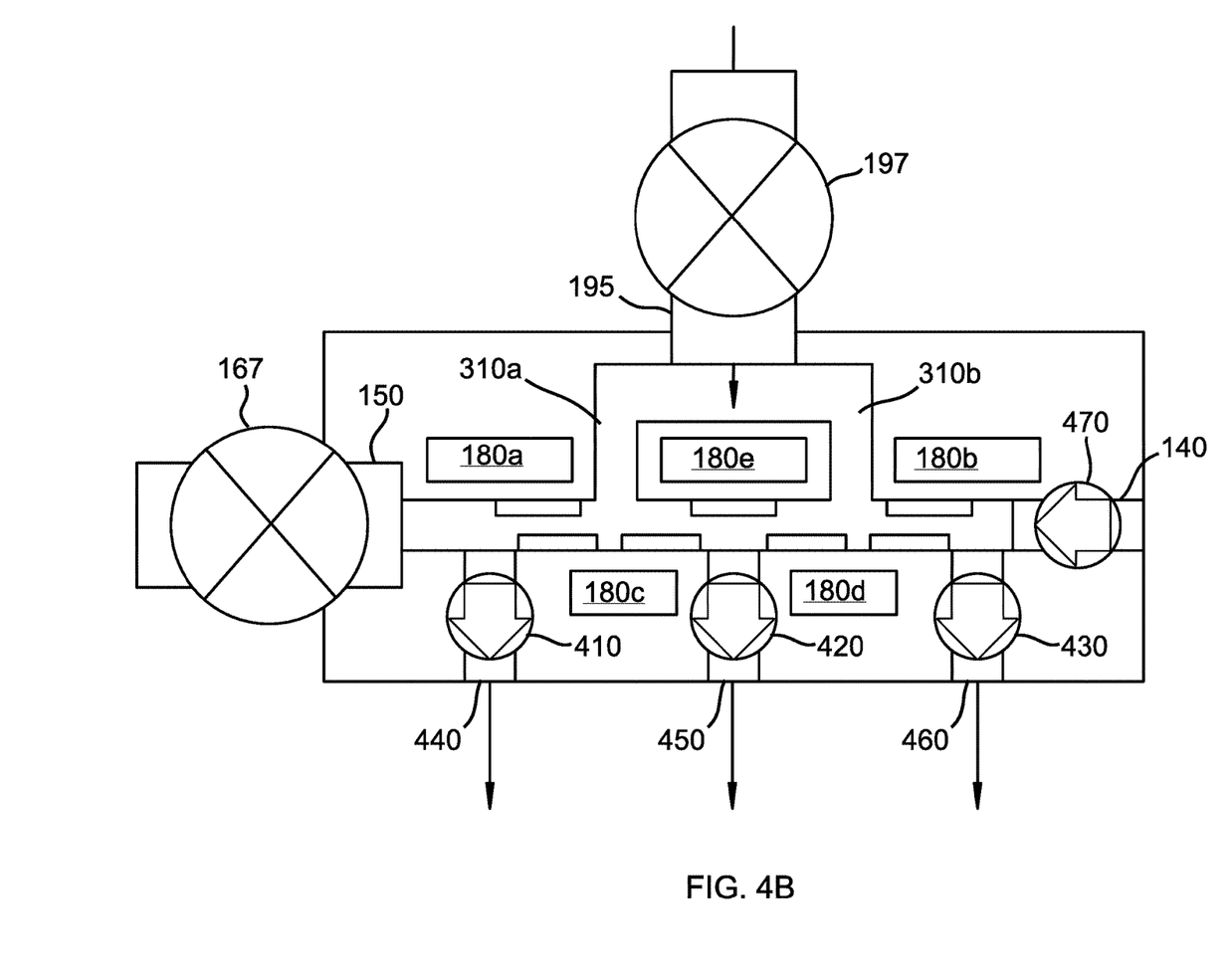
FIG. 4B illustrates a cross sectional view of the embodiment of FIG. 4B during the exhausting step.

FIG. 4B illustrates the embodiment of FIG. 4A during the subsequent exhausting step. Arrows illustrate the flow of moving phase gas through moving phase port 195 into the conduit. Similar to the embodiment of FIG. 3, multiple channels, illustrated as channels 310a and 310b in FIG. 4B, lead from moving phase port 195 into the conduit. The volatile analytes desorb from the sorbents into the moving phase gas and exit through gas analysis columns 440, 450, and 460. Note that the embodiment of FIGS. 4A and 4B include thermal insulating material 180a, 180b, 180c, and 180d within the walls of the conduit so that heat may be used to assist the desorption of each section individually into the nearest gas analysis column.

Figure 5A:
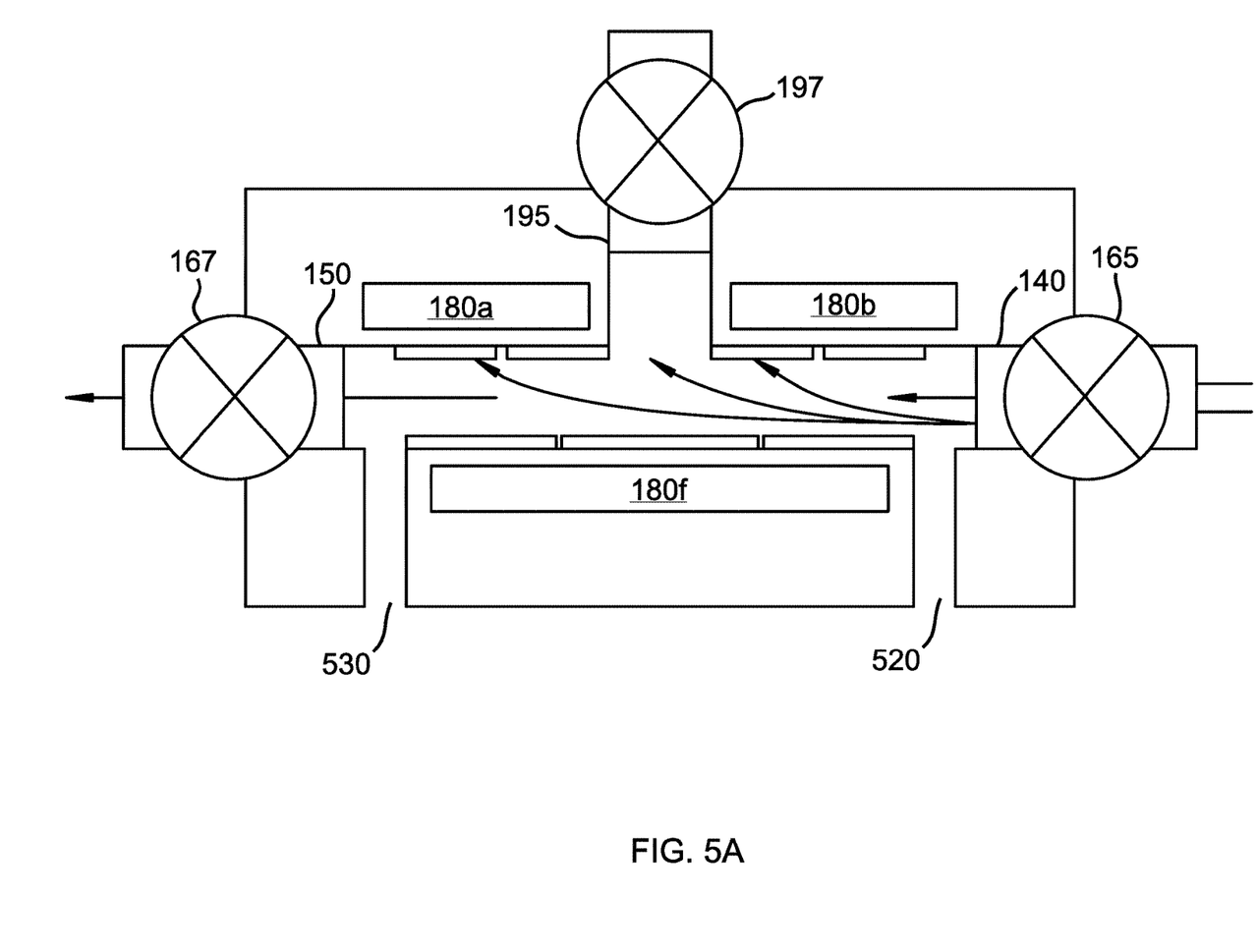
FIG. 5A illustrates an embodiment of the device which includes all external valves during the preconcentration step.

FIG. 5A illustrates an embodiment of the device which includes all external valves. The device is shown during the preconcentration step. Arrows illustrate the direction of flow through the conduit. Sample is injected into entrance port 140 and the volatile analytes adsorb to the sorbents. The remaining material in the sample exits through exhaust port 150. Moving phase port 195 includes moving phase valve 197, entrance port 140 includes valve 165, and exhaust port 150 includes valve 167. Each valve is external to the conduit. The embodiment of FIG. 5A further includes gas analyzer port 520 and gas analyzer port 530. There are no valves in gas analyzer ports 520 and 530. When in use, a weak vacuum may be used to draw the flow of material from the headspace. The resistance in the conduit is high and limits the in-flow from the columns through the gas analyzer ports while preconcentration is occurring. The high resistance in the GC columns also reduces diffusion of volatile analytes into the GC columns during preconcentration. For at least this reason, no internal valves are needed in this embodiment.

Figure 5B:
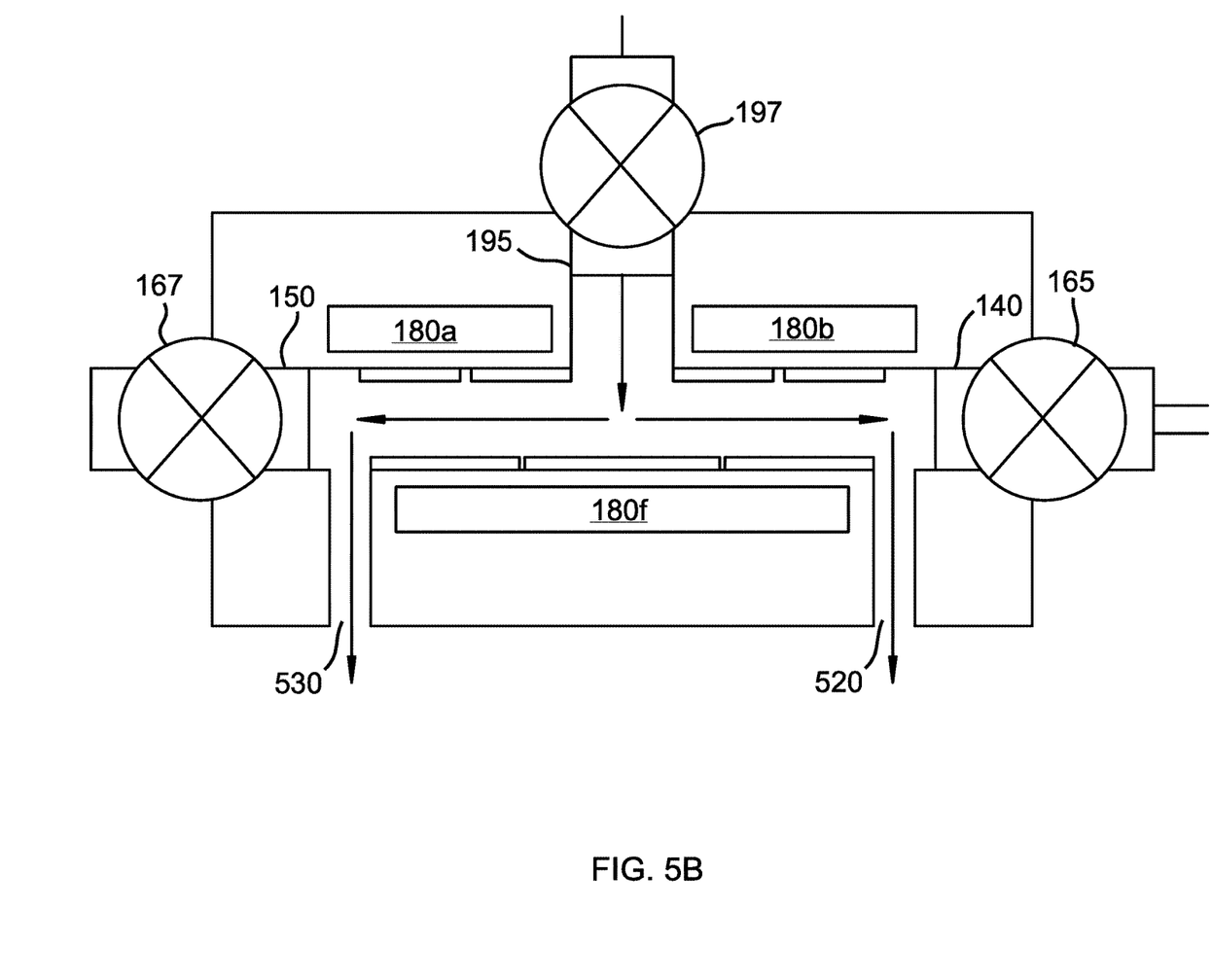
FIG. 5B illustrates a cross sectional view of the embodiment of FIG. 5B during the exhausting step.

FIG. 5B illustrates the embodiment of FIG. 5A during the exhausting step. Pressure is created when moving phase gas is injected through moving phase port 195. The moving phase gas is diverted in both directions through both sections of the conduit. Volatile analytes that are adsorbed to sorbents desorb as the moving phase gas passes over them. The moving phase gas carries the desorbed volatile analytes through the nearest gas analyzer port. Because of the direction of moving phase gas flow, the volatile analytes from one section to not revert back along the column into the other section and out the gas analyzer port connected to that section. Consequently, volatile analytes adsorbed to a particular sorbent are diverted into the proper GC column for their separation. Note that the device of FIGS. 5A and 5B includes thermal insulating material 180a, 180b, and 180f. Accordingly, heat may be used to sequentially desorb the volatile analytes in each section as described elsewhere herein.

Figure 6A:
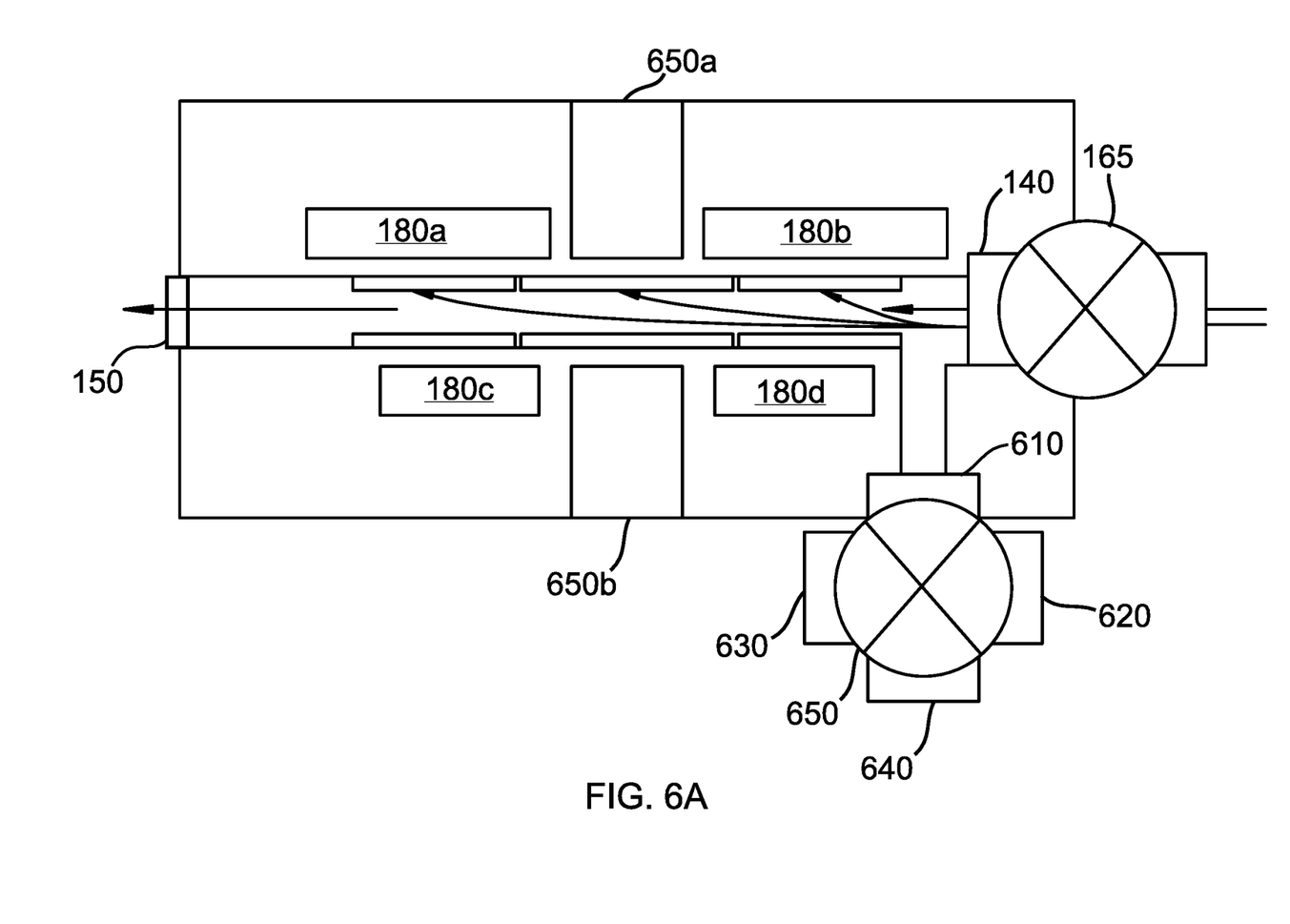
FIG. 6A illustrates another embodiment of the device during the preconcentration step.

FIG. 6A illustrates an embodiment of the invention during the preconcentration step. In the embodiment shown in FIG. 6A, sample is being injected through entrance port 140. In this embodiment, entrance port 140 includes valve 165 which is an external valve. The volatile analytes in the sample adsorb to the different sorbents as the sample travels along the conduit. The remainder of the sample exits the conduit through exhaust port 150. In this embodiment, a weak vacuum is used to draw the flow of sample through entrance port 140 from the headspace. A four-way pipe comprises gas analyzer port 620, gas analyzer port 630 each of which may be connected to a different GC column. The four-way pipe also includes moving phase port 640 which may be used to inject moving phase gas into the device and into the GC columns as described in more detail below and illustrated in FIG. 6D. Valve 650 controls the differential flow between the different ports associated with the four-way column. Note that four-way pipes and t-connector pipes may be used to combine the various ports described herein according to the disclosure and may be combined with any of the embodiments described herein.

Figure 6B:
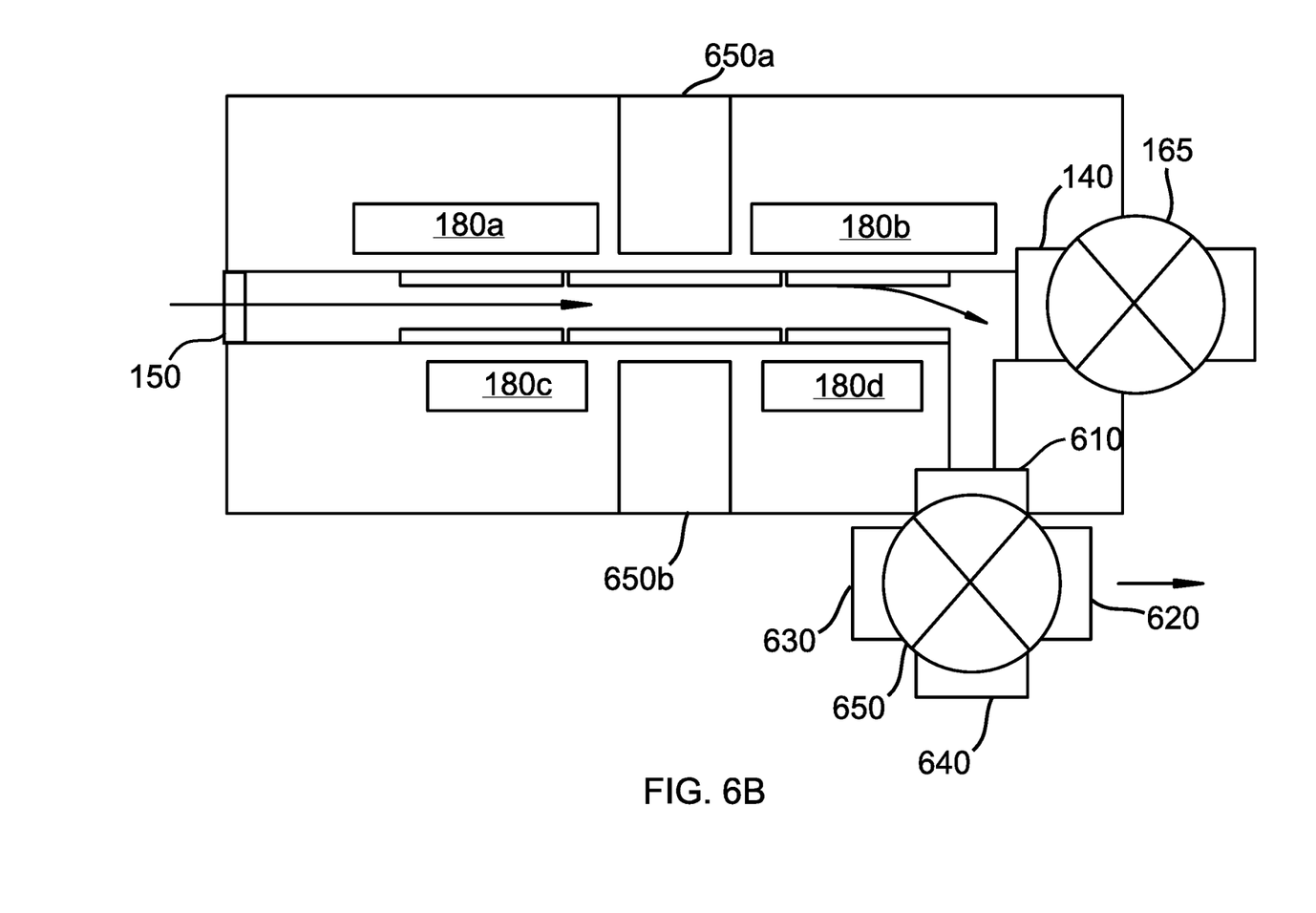
FIG. 6B illustrates the embodiment of FIG. 6A during a first exhausting step.

FIG. 6B illustrates the embodiment of FIG. 6A during a first exhaust step. As shown by the arrows which depict the flow of material through the conduit, a vacuum draw is used to reverse the flow from exit port 150 toward entrance port 140. Valve 165 may be closed so that material may not escape through entrance port 140. Note that the embodiment of FIGS. 6A-D include thermal insulating material 180a, 180b, 180c, and 180d. In addition, a thermal barrier is created between the two sections of the conduit by thermal insulating material 660a and 660b. In some embodiments, the substrate may comprise thermal insulating material. In the first exhaust step, the second section (closest to entrance port 140) is heated which enhances the desorption of volatile analytes from the sorbents in the second section (nearest entrance port 140). Valve 650 is positioned so that gas analyzer port 620 is open and gas analyzer port 630 is closed to the flow of material. Consequently, the volatile analytes that were adsorbed to sorbents in the second section enter the GC column connected to gas analyzer port 620 but not gas analyzer port 630. Additionally, moving phase port 640 may be closed to material flow.

Figure 6C:
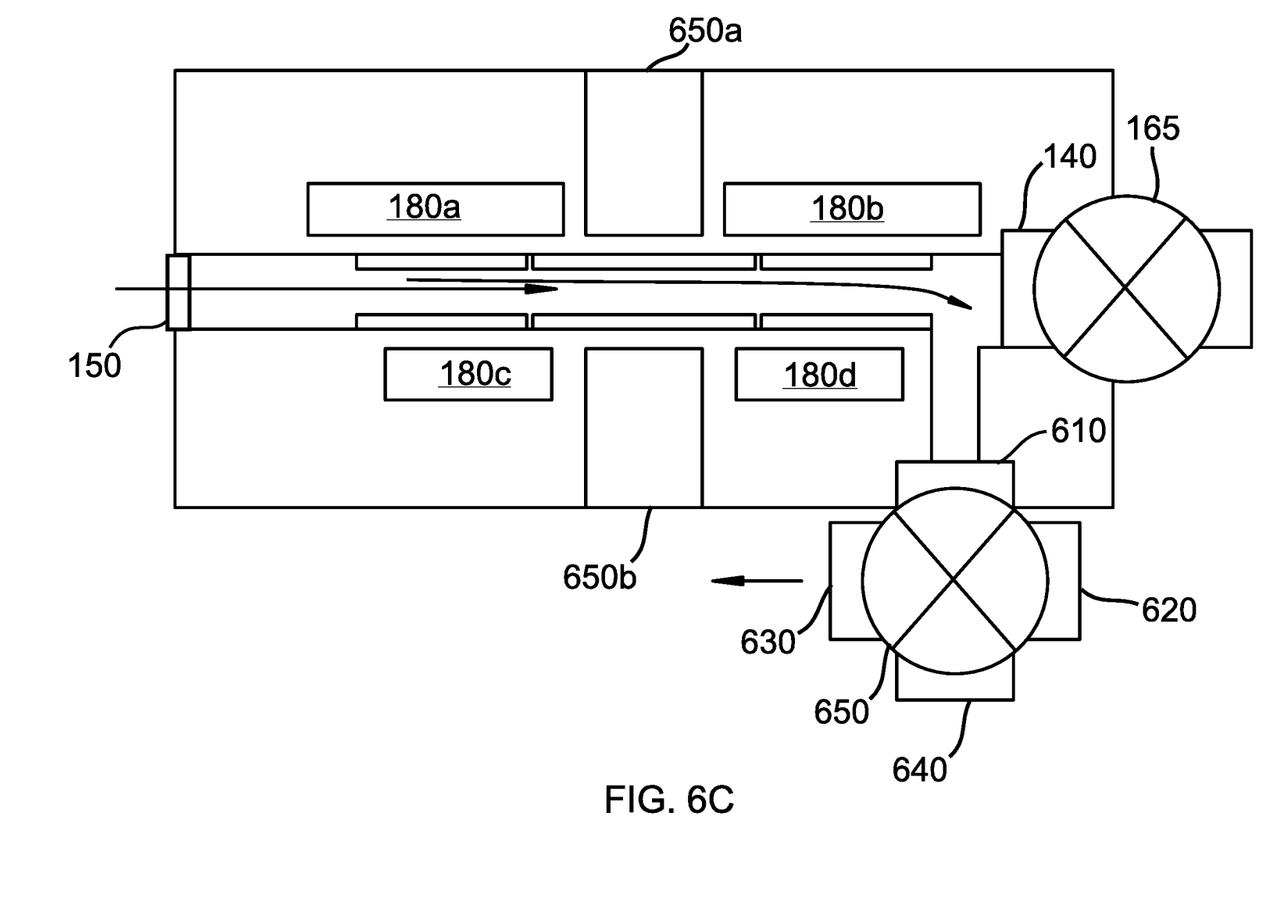
FIG. 6C illustrates the embodiment of FIG. 6A during a second exhausting step.

FIG. 6C illustrates the embodiment of FIG. 6A undergoing a second exhaust step. In this exhaust step, the first section of the conduit (nearest exit port 150) is heated which enhances the desorption of volatile analytes from the sorbents in the first section. The weak vacuum causes the recently desorbed volatile analytes from the first section to travel through the conduit and out through gas analyzer port 630. Valve 650 may be positioned such that gas analyzer port 620 and moving phase port 640 are blocked. Consequently, the volatile analytes that were adsorbed to sorbents in the first section enter the GC column connected to gas analyzer port 630 but not gas analyzer port 620.

Figure 6D:
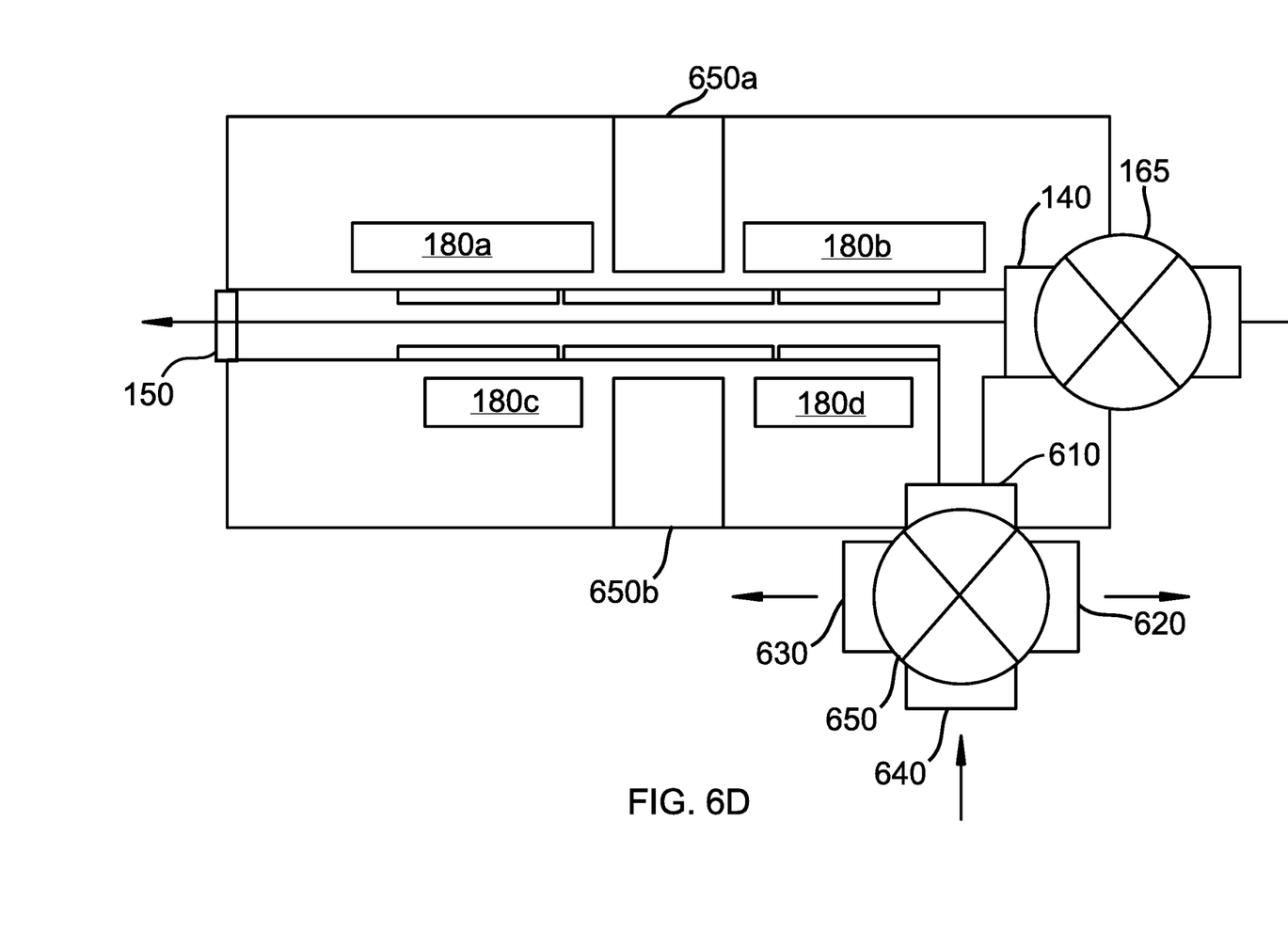
FIG. 6D illustrates the embodiment of FIG. 6A during a GC analysis and conduit purging step.

FIG. 6D illustrates the embodiment of FIG. 6A during a purge step. To purge the conduit, valve 165 is actuated such that gas may travel through entrance port 140, through the length of the conduit, and out through exit port 150.

Alternatively, FIG. 6D illustrates how valve 650 may be actuated to inject moving phase gas through moving phase port 640 into the GC columns that may be connected to gas analyzer ports 620 and 630 during a GC run. In this process, valve 650 is positioned such that moving phase port 640 and gas analyzer valves 620 and 630 are open. Gas is injected through moving phase port 640 and through gas analyzer valves 620 and 630 as indicated by the arrows in FIG. 6D. Entrance port 610 may be closed at this point to prevent moving phase gas from re-entering the conduit. Alternatively, entrance port 610 may be open to simultaneously purge conduit while conducting a GC analysis.

While specific embodiments are illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A microfabricated device for extracting and preconcentrating volatile analytes prior to gas chromatography comprising:
    a conduit, the conduit comprising:
        a first section, the first section comprising:
            a first section wall, the first section wall comprising a microfabrication substrate, a first section outer surface, and a first section inner surface, wherein the first section inner surface is coated with a first sorbent, and wherein the first sorbent comprises a first binding affinity for volatile analytes;
            an entrance port; and
            a first gas analyzer port, the first gas analyzer port comprising a first valve;
        an intermediate section, the intermediate section comprising a microfabrication substrate, an intermediate section outer surface, an intermediate section inner surface, and a moving phase port, the moving phase port comprising a moving phase valve;
        a second section, the second section comprising:
            a second section wall, the second section wall comprising a microfabrication substrate, a second section outer surface, and a second section inner surface, wherein the second section inner surface is coated with a second sorbent, and wherein the second sorbent comprises a second binding affinity for volatile analytes;
            an exit port; and
            a second gas analyzer port, the second gas analyzer port comprising a second valve,
        a thermal insulating material, wherein the thermal insulating material is positioned within the first section wall, the intermediate section wall, and the second section wall at a point of intersection between the first section and the intermediate section and between the intermediate section and the second section;
    wherein the first section, intermediate section, and second section are connected linearly.

2. The device of claim 1, wherein the exit port is positioned on either the first section or the second section.

3. The device of claim 1, wherein the entrance port and the first gas analyzer port are combined in a t-connector pipe, and wherein the first valve is positioned within the t-connector pipe such that the first valve diverts material through the entrance port when the first valve is in a first position and from the conduit through the first gas analyzer port when the first valve is in a second position.

4. The device of claim 1, wherein the exit port and second gas analyzer port are combined in a t-connector pipe, and wherein the second valve is positioned within the t-connector pipe such that the second valve diverts fluid from the conduit through the exit port when the second valve is in a first position and from the conduit through the second gas analyzer port when the second valve is in a second position.

5. The device of claim 1, wherein the first section is coated with a third sorbent, and wherein the third sorbent comprises a third binding affinity for volatile analytes that is different from the first binding affinity and different from the second binding affinity.

6. The device of claim 1, wherein the second section is coated with a fourth sorbent, and wherein the fourth sorbent comprises a fourth binding affinity for volatile analytes that is different from the first binding affinity, the second binding affinity, and the third binding affinity.

7. The device of claim 1, wherein the conduit further comprises at least three gas analyzer ports.

8. The device of claim 7, wherein each of the at least three gas analyzer ports comprises a valve.

9. The device of claim 8, wherein each of the valves is independently selected from the following: a check valve and an actuated valve.

10. The device of claim 1, further comprising a section valve, wherein the section valve is positioned within the conduit between the first section and the second section and wherein the section valve blocks volatile analyte movement between the first section and the second section when the section valve is in a first position and allows volatile analyte movement between the sections when the section valve is in a second position.

11. The device of claim 10, wherein the section valve is selected from the following: a check valve and an actuated valve.

12. The device of claim 1, further comprising a first conduit heater, wherein the first conduit heater is thermally connected to the first section.

13. The device of claim 12, wherein the first conduit heater is independently and thermally connected to the first section and the second section to heat the first section and the second section independent of each other.

14. The device of claim 1, further comprising a second conduit heater, wherein the second conduit heater is thermally connected to the second section.

15. The device of claim 1, wherein the entrance port, the first gas analyzer port, the second gas analyzer port, and the moving phase port are combined in a four-way pipe.

16. The device of claim 15, wherein a four-way valve functions as the first valve, the moving phase valve, and the second valve, and wherein the four-way valve is positioned within the four-way pipe.

17. The device of claim 1, wherein the thermal insulating material comprises one of more of the following: plastic, glass, and insulating ceramic.

18. The device of claim 1, wherein the substrate comprises one or more of the following: glass, quartz, ceramic, silicon, photopatternable glass, and photopatternable ceramic.

19. The device of claim 1, wherein the inside diameter of the conduit is less than about 0.5 mm.

20. The device of claim 19, wherein the inside diameter of the conduit is less than about 0.25 mm.

* * * * *